United States Patent [19]

Van Wagenen

[11] Patent Number: 4,676,639

[45] Date of Patent: Jun. 30, 1987

[54] GAS CELL FOR RAMAN SCATTERING ANALYSIS BY LASER MEANS

[75] Inventor: Richard A. Van Wagenen, Salt Lake City, Utah

[73] Assignee: Biomaterials International, Inc., Salt Lake City, Utah

[21] Appl. No.: 821,349

[22] Filed: Jan. 22, 1986

[51] Int. Cl.[4] .................... G01J 3/44; G01N 21/05
[52] U.S. Cl. .................................... 356/246; 356/301
[58] Field of Search ............... 356/301, 318, 246, 338, 356/339

[56] References Cited

U.S. PATENT DOCUMENTS

| | | | |
|---|---|---|---|
| 4,088,407 | 5/1978 | Schoeffel et al. | 356/246 |
| 4,200,802 | 4/1980 | Salzman et al. | 356/318 |
| 4,440,497 | 4/1984 | Carey et al. | 356/246 |
| 4,606,636 | 8/1986 | Monin et al. | 356/338 |

OTHER PUBLICATIONS

Weber et al., *Journal of the Optical Society of America*, vol. 57, No. 1, Jan. 1967, pp. 19-28.
Skogen Hagenson et al. *The Journal of Histochemistry and Cytochemistry*, vol. 25, No. 7, 1977, pp. 784-789.

Primary Examiner—F. L. Evans
Attorney, Agent, or Firm—Thorpe North & Western

[57] ABSTRACT

A sample gas cell and casing system for use in sampling and analysis of gas samples by Raman light scattering comprises a tubular casing means forming a longitudinal bore, a gas sampling cell transversely mounted in the tubular casing means relative to the longitudinal bore with the gas sampling cell protruding at either end through the tubular casing. The gas cell has opposing windows at the ends which are located outside the tubular casing and are interconnected by a continuous sidewall passing through the casing. The end windows and sidewall define a longitudinal gas chamber having an axis perpendicular to the axis of longitudinal bore in the tubular casing. At least a portion of the continuous sidewall located inside the casing has window means through which scattered light may pass. The cell further contains inlet and outlet means communicating with the chamber to pass a sample gas through said cell. Light collection and/or reflection means are located relative to the side window means to collect and/or reflect Raman scattered light passing through the sidewall window means to a detection system.

7 Claims, 4 Drawing Figures

GAS CELL FOR RAMAN SCATTERING ANALYSIS BY LASER MEANS

BACKGROUND OF THE INVENTION

This invention relates to a gas sampling cell for use in the near simultaneous analysis of multiple gases by means of Raman scattering wherein the Raman scattering sample is contained in a cell placed within the laser resonator. More specifically, this invention relates to a gas cell unit for use in the detection of multiple respiratory and anesthesia gases by Raman scattering wherein the incident laser beam passes through the gas sample contained in the cell which is preferably placed in the intracavity of a laser. However, the cell could also be used for extra cavity laser Raman gas determinations.

A proposed method for use in monitoring several gases in critical care situations is based on Raman light scattering. The Raman light scattering effect relies on the interaction of monochromatic light with the vibrational/rotational modes of molecules to produce scattered light which is frequency shifted from that of the incident radiation by an amount corresponding to the vibrational/rotational energies of the scattering molecules. Since these energies are species-specific, an analysis of the various frequency components present in the Raman scattering spectrum provides chemical identification of the gases present in the scattering volume. The intensity of the various frequency components or Raman lines provides quantitation of the gases present providing suitable calibrations have been made. The relative sensitivity to the different gases remains absolutely fixed, eliminating frequent calibration requirements.

Raman techniques have been widely used for atmospheric monitoring and for combustion applications. Sensitivities better then 1 ppm have been demonstrated. Typical application of Raman scattering analysis coupled with computer assisted signal processing techniques is reported in Lapp et al., "Laser Raman Gas Diagnostics", Plenum Press, New York. London, 1974.

Raman scattering analytical techniques are also described in the patent literature. Chupp, U.S. Pat. No. 3,704,951 teaches laser Raman spectroscopy utilizing a sampling cell with a multi-pass configuration. A laser beam enters into the cell configurations of concave mirrors facing each other such that there is a multiple reflection of the laser beam between the mirrors to accomplish the required optical power density enhancement in the sampling area and subsequent signal enhancement. This device and accompanying technique is limited in that it provides for analysis through only a single detector. Hence, simultaneous monitoring of multiple gases is not possible. Moreover, this device is intended for use primarily with liquids and has only limited application for gases. Also, the alignment of the mirrors for optimal signal is exceedingly delicate. Finally, the beam size in the sampling region must be quite small to maintain low sample volume and subsequently high signal response time. A multimirror approach makes this difficult, if not impossible, given the optics of such a system.

Hatzenbuhler, U.S. Pat. No. 3,807,862 also teaches a specific application of Raman spectroscopy in which a fluid sample is subjected to a laser beam and only a single Raman line is evaluated. In other words, there is no teaching of a technique for the determination of multiple gases.

Leonard, U.S. Pat. No. 3,723,007 is drawn to a method for the remote sensing of gas concentrations through use of a high-energy pulsed laser and a mirror telescope, using a grid polychromator. This system requires a laser output in the 10 kW range and is unsuitable for general application. Moreover, the use of an expensive spectrometer presents an obstacle in the way of cost-beneficial production of the device.

A more recent and effective system for the simultaneous detection of multiple gases is taught in Albrecht, et al., German Pat. DE No. 27 23 939 C2. This patent also utilizes a multi-pass cell to constrain the laser radiation in a region between two concave mirrors for signal enchancement but utilizes an unpolarized laser beam to provide a 360° monitoring geometry for the Raman scattered light. A series of six detectors, each accompanied by an interference filter comprised of one broadband and one gas-specific filter, are provided to collect six separate Raman lines for the simultaneous monitoring of six different gas components. This method, while monitoring multiple gases simultaneously, requires six separate detectors including separate photomultiplier tubes and recording instruments. Such a complex system is bulky and expensive. Moreover, since the orientation of the six detectors described in the German patent could not be expected to exactly image in the same area, the acquisition of all gas concentrations could not be from exactly the same point in the gas flow stream.

A method and system for the near simultaneous monitoring and analysis of multiple gases which avoids the use of multiple detectors is disclosed in an application entitled "Molecular Gas Analysis By Raman Scattering In Intracavity Laser Configuration" filed Sept. 11, 1985 as Ser. No. 774,643. The present inventor is one of the joint inventors of that application which discloses a gas cell and outer casing for use in the intracavity laser sampling and analysis technique. That cell and casing is the sole invention of this inventor and forms part of the subject matter of this application.

OBJECTS AND SUMMARY OF THE INVENTION

It is an object of the present invention to provide a sampling cell and casing unit for intracavity use within a laser system for the near simultaneous monitoring of multiple gases by means of Raman scattering.

It is also an object of this invention to provide a gas sampling cell for location within the resonance cavity of a laser to enhance the optical power available within the sampling volume of the cell and still provide for small sample volume and continuous sampling.

A still further object of this invention is to provide a gas sampling cell which is also suitable for extra cavity use in a similar laser system for gas analysis based upon Raman scattering.

Another object of this invention is to provide a unit consisting of a casing housing a gas cell and means for the collection and redirection of the scattered light into collection and detection means.

These and other objects are made possible by means of a gas sampling cell and surrounding casing means preferably adapted to be located within the resonance cavity of the laser with the cell being constructed with appropriate windows and mirror elements to provide for the enhancing, directing and collection of the Raman scattering signal. When using a single detector, a reflection mirror is located within the cell casing adjacent to the gas cell and normal to the gas cell axis along which the laser beam will travel. The reflection mirror is used to capture some proportion of the Raman scattered light solid angle and direct it from the cell casing towards the collection and detection portions of the overall system. If desired, alignment means may be located within the casing to provide for bringing the gas cell into optimal alignment with the laser beam and collecting and redirecting scattered light into collection lens means for passage into a filtering and detection system as taught in Ser. No. 774,643.

DETAILED DESCRIPTION OF THE INVENTION

Figure 1:
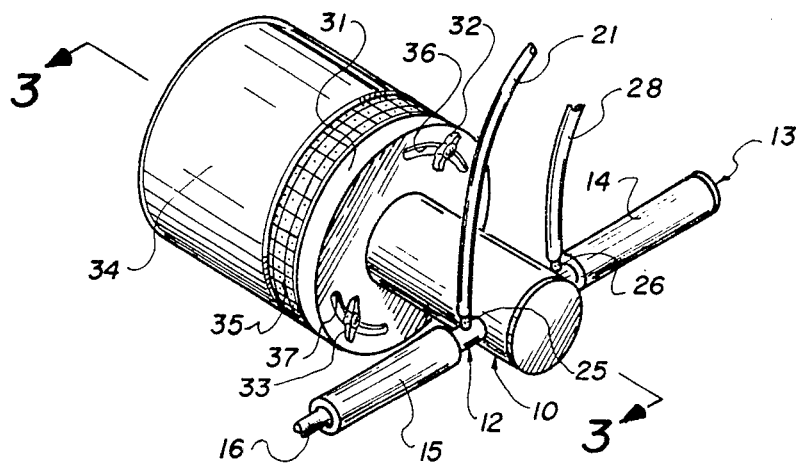
FIG. 1 is a perspective view of one embodiment of the invention showing the casing housing an intracavity gas sampling cell, reflection mirror and containing means for aligning the gas cell with the scattered light collection means.
Figure 2:
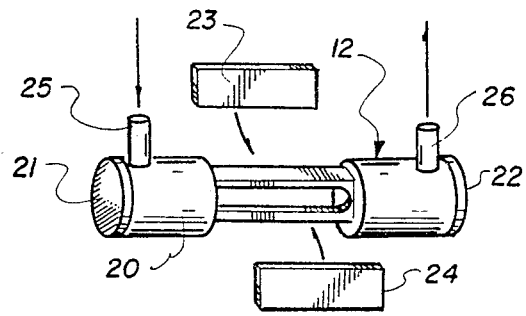
FIG. 2 is a perspective view of the gas sampling cell as contained in the casing shown in FIG. 1 but having the side windows removed.
Figure 3:
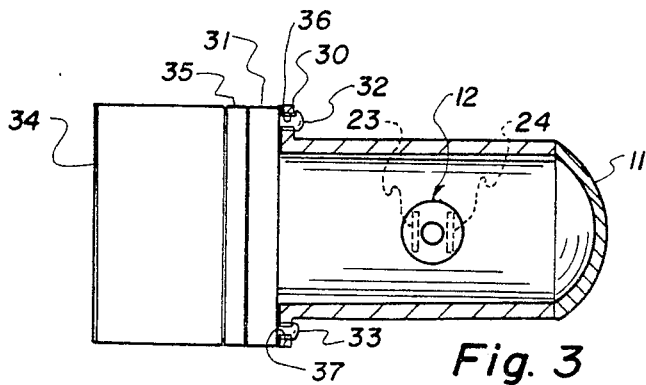
FIG. 3 is a side cross-sectional view of the gas cell and casing taken along lines 3—3 of FIG. 1.

There is shown in FIGS. 1-3 one complete and preferred embodiment of the invention.

An overall system in which this embodiment of the gas cell may be utilized is fully disclosed in pending application Ser. No. 774,643 mentioned above and broadly consists of a laser which directs a polarized laser beam, such as a cw Ar+ laser (tens of milliwatts extracavity power at 488 nm) into the sampling gas cell (hereinafter described) containing the gases to be analyzed all located within the resonating cavity of the laser.

Although the gas cell of this invention may also be utilized extra cavity, there are at least two advantages to be gained by placing the sample gas cell within the laser resonator. The intracavity laser power is immediately higher than the extracavity laser power by a factor of $[1+R]/T$, where R and T are the reflectivity and transmission of the laser output coupler mirror located at the end of the laser resonance cavity. The other advantage is obtained by increasing the reflectivity of the output mirror to further enhance the circulating intracavity power. An intracavity laser Raman spectrometer, although somewhat different from that disclosed in Ser. No. 774,643, is described by Hercher, et al., "Applied Spectroscopy", Vol. 32, No. 3, (1978) pp. 298-301.

The power of the intracavity laser beam interacting with the gas molecules can thus be enhanced by a factor of about 100 within the intracavity gas cell over the extracavity to provide the necessary high excitation intensity within the scattering volume at the center of the gas cell. The Raman scattered light, which is emitted nonisotropically within the cell, is then collected over as large a solid angle as possible by a collection lens located perpendicular to the axis of the cylinder formed by the incident laser light as described in Ser. No. 774,643. Such a lens may be either a cylindrical or circular lens. A reflection mirror (hereinafter described) within the casing housing the gas cell captures and redirects a proportion of the Raman scattered light back into the collection lens and serves to increase the collection of Raman scattered light by a factor of almost two.

The collection lens and reflection mirror function optimally to collect light from a point in the laser beam assuming the collection lens is a spherical lens and the reflection mirror is a spherical mirror. Light collection from a specified point with good stray light rejection, if desired, may be facilitated by use of an iris diaphram (not shown) optimally placed in the gas cell (as described in Ser. No. 774,643) to reject light from all other areas of the laser beam. The iris functions basically as a baffle to reject stray light. As will be described in connection with FIG. 4, such baffles could be oriented throughout the interior of both the casing and the gas cell to reduce stray light which adds to the background signal. The use of a cylindrical reflection mirror in conjunction with an approxpriately oriented cylindrical collection lens will also function to redirect a proportion of the total solid angle of scattered light from the complete length of the laser beam sampled rather than from a point as with a spherical mirror-spherical lens combination.

Both the reflection mirror and collection lens must be properly aligned with respect to the laser beam in order to obtain optimal results.

At one end of an ion laser's resonant cavity, adjacent to the plasma tube with Brewster window, is a high refectivity planar mirror on a prism which is used for wavelength selection. An air tight sleeve generally surrounds the mirror-prism and Brewster window on the end of the plasma tube to protect these components from particulate and molecular contamination. At the opposite end of the plasma tube is another Brewster window. The two Brewster windows function to transmit the prism selected polarized wavelength of the laser beam being pumped through the resonating cavity of the laser without substantial loss. Such a configuration is described in detail in Ser. No. 774,643.

The remainder of the laser cavity is pertinent to the present invention and is shown in FIG. 1.

FIG. 1 shows a casing 10 housing a gas cell 12. An output coupler mirror 13 forming the end of the laser resonance cavity is connected by a sleeve 14 to the gas cell 12. At the opposite end of the gas cell 12 a sleeve 15 connects the plasma tube 16 with gas cell 12. The sleeves are present to prevent dust or other contamination from entering into the resonance chamber and subsequently fouling mirrors and windows causing a subsequent attenuation of intracavity resonance and loss of power. The plasma tube, sleeves and output coupler mirror, while necessary to the operation of the Raman scattering techniques disclosed in Ser. No. 774,643 are not per se part of the present invention. However, since the resonance cavity of the laser is located between two mirrors, one mirror (not shown) comprising one side of a prism as above described adjacent to the end of plasma tube 16 opposite the end shown in FIG. 1, and the other mirror being an output coupler mirror 13, the placement of gas cell 12 between the end of plasma tube 16, shown in FIG. 1, and mirror 13 is termed "intracavity".

One embodiment of a gas sampling cell 12 is shown in detail in FIG. 2 and consists of a framework having a hollow interior, means for bringing a gas sample into and out of the interior and windows through which both the incident laser beam and the scattered Raman light may pass. The shape, i.e. cylindrical, rectangular, etc., is not important as long as the functional criteria are met. The cell shown consists of a hollow housing 20 generally cylindrical in shape having its axis oriented to accomodate the passage of the laser beam through the axial center. At either end of the housing are optical windows 21 and 22. Windows 21 and 22 are coated with a highly efficient narrow band antireflection coating, i.e. a "V"-coating, for the particular wavelength of the laser. "V"-coatings are multilayer antireflection coatings which reduce the reflectance of an optical component to near-zero for a very specific narrow wavelength range and are generally intended for use at normal or near normal incidence or at some well specified incidence angle. Hence, windows 21 and 22 are approximately parallel to each other and substantially normal to the axis of the housing and the laser beam. In this embodiment, maximum intracavity power is achieved if windows 21 and 22 are slightly tilted to be non-normal to the laser beam. By slightly tilted is meant that the windows do not vary more than about 5° in either direction from a position perpendicular to the laser beam. Hence the term "substantially normal" is used. The windows, if tilted, will preferably be tilted in the same direction so as to remain parallel to each other. Such V-coating will achieve maximum relfectances of not more than about 0.25% per interface and are generally effectie to allow only about 0.1% reflectance per interface at the specified wavelength. Thus, they do not appreciably interfere with the transmittances of the laser beam through the resonating cavity of the laser. The purpose of windows 21 and 22 is two-fold; first, they constrain the sample gas within cell 12 and thus minimize sample volume and maximize response time, and, second, they serve to isolate both the Brewster window located at the end of plasma tube 16 and the output mirror 13 from possible contamination arising from the gas sample.

The preferred end window orientation of the gas cell for a Raman gas analysis system is to utilize the essentially parallel end windows, each oriented essentially perpendicular to the laser beam so as to be within the stated angular tilt parameters. This preserves both the polarization and alignment of the laser beam when the cell is positioned between the Brewster window and a spherical surfaced output coupler mirror. Such windows need to be coated with an extremely efficient antireflection coating such as the V notch coating described which is specific for the particular laser line of interest. Windows essentially perpendicular to the laser beam endow the gas cell with substantial insensitivity to changes in the refractive index of various gas samples entering the gas cell. That is, for any uniform gas sample in the cell, the laser beam passes directly through the cell intercepting both windows essentially perpendicularly. However, of most importance, the laser beam is not refracted or deflected within the cell or the windows such that it intercepts the nonplanar output coupler mirror in a non-optimal position resulting in an attenuation of laser power in the intracavity region accompanied by a subsequent loss of Raman scattering signal.

Less preferred, but perhaps functionally adequate, means of making a gas cell for Raman gas analysis could utilize end windows oriented at some non-normal angle to the incident laser beam. One such means would be to orient the windows at Brewster's angle to perserve the polarization of the laser beam. Such windows would not have to be antireflection coated in this particular orientation. However, minute changes in gas composition within the cell result in refractive index changes sufficient to cause refraction and subsequent laser beam deflection to a non-optimal alignment with the nonplanar output coupler mirror. This results in an altered mode structure within the resonant cavity with a subsequent loss of intra cavity power and attenuation in signal. One means to compensate for this would be to continuously monitor the output or extracavity laser power using a suitable detector. Assuming that the only factor causing output power changes and thus intracavity power changes is the refractive index change resulting from change in sample gas composition, one may be tempted to use the ratio of the original calibrated power to the measured extracavity power to correct for refractive index changes arising from different gas samples. In reality, however, other factors can also affect the output power such as effects on the detector, contamination of output coupler mirror, gas cell windows or Brewster windows, etc. All of these must be taken into consideration. Also, refractive index changes could cause displacements to the intracavity laser beam in the gas cell thus leading to errors in the Raman signal. The same argument may be extended to other end window orientations.

One attractive alternative to that discussed above would be to configure the laser's resonant cavity such that an intracavity gas cell with windows oriented at Brewsters angle was situated between the Brewsters windows of the plasma tube and a planar output coupler mirror. This would preserve the polarization state, eliminate the need for a "V" notch antireflection coating and make the resonant cavity gas cell optics much more insensitive to change in sample refractive index because no matter where the beam intercepts the output coupler mirror it would be at normal incidence as opposed to non-normal incidence on a spherical mirror.

The hollow housing 20 at the central portion of the cell also contains optical side windows 23 and 24. The alignment of these windows is not as critical as the optical end windows 21 and 22. However, they are preferably parallel to each other. These optical side windows may also be coated with a broad band antireflection coating. Since these windows must transmit the Raman scattered light to both the reflection mirror and collection lens they must pass the desired wavelengths. Hence, a high efficiency broad band antireflection coating such as HEBBAR(tm) is appropriate. Broad band coatings are multilayer dielectric films, comprising alternate layers of various refractive index transparent materials, combined in such a way to reduce the overall reflectance to an extremely low level for the spectral range covered. Over the broad band range the reflectance will not generally exceed 1.0% and will generally be below 0.6%. The cell contains an inlet 25 and an outlet 26 for passing the sample gas through the cell. The cell design is very important in that it allows for a very small volume of gas, typically between about 0.1 and 1.0 cubic centimeters, to constantly be passed through the laser beam. On the other hand, it is well adapted for use in a batch type operation in that only a small sample is required of any given gas to be analyzed. As shown in FIG. 1, inlet 25 is connected via supply line 27 to a solenoid valve (not shown) and sample gas is drawn into the cell interior by means such as an air pump. Tubing 28 connected to cell outlet 26 conveys sampled gas out of the cell for disposal or reintroduction into a patient's airway or for collection and storage.

The gas cell 12 is also part of the Raman scattered light collection system and is located within casing 10 as shown in FIGS. 1 and 3. The interior of casing 10 contains gas cell 12 oriented such that its axis will be parallel to and coincidental with the intracavity laser beam. Casing 10 is tubular and is oriented such that its axis will be perpendicular to the laser beam. One end of casing 10 consists of reflection mirror 11 which may be spherical or cylindrical in shape. The opposite end of casing 10 fits inside of and is affixed to an alignment ring 30 by welding, adhesives or other appropriate means. Alignment ring 30 has two arcuate slots 36 and 37 completely penetrating its thickness and can be tightly secured to an interface ring 31 via two threaded bolts 32 and 33 which extend through the slots. This allows casing 10 to be rotated about its axis and thus tilted slightly so as to align the gas cell 12 with respect to the laser beam for optimal intracavity power. Having attained the optimal power, bolts 32 and 33 are tightened, locking casing 10 and gas cell 12 into place in relation to the laser beam and also to collection lens 34. Interface ring 31 is attached securely to collection lens 34, via a standard bayonet ring mount 35 common to most single lens reflex 35 mm cameras or other similar lens means. This combination of gas cell casing, interface ring, bayonet ring and camera lens may then be attached to a filter wheel as detailed in Ser. No. 774,643. Casing 10 may also house the necessary collection lens(es) and filters as taught in Ser. No. 774,643.

It is important that the gas cell be properly aligned and fixed in position to attain the optimal signal. The above described means is only one way of accomplishing certain optical alignments. The following four alignment parameters are essential if optimal results are to be obtained. (1) The casing, gas cell, collection lens(es) and/or reflection mirror must be vertically aligned with respect to the laser beam. (2) The distance of both collection (lens(es) and reflection mirror must be located at a specified distance from the laser beam and along an axis perpendicular to the laser beam. For collection lens(es) that distance is equal to the focal length of the lens. For a reflection mirror, the distance from the laser beam is equal to the radius of curvature of a circular or cylindrical mirror. (3) The angular tilt of the gas cell around both axes perpendicular to the laser beam must be fixed to optimize the angle of incidence of the laser beam on the end windows of the cell. (4) The rotation of the gas cell, and hence the gas cell end windows, around the axis of the laser beam must be fixed.

These adjustments may be made and components fixed securely in place at the time of installation of the cell 12 in casing 10 by any suitable mechanical or chemical means such as set screws, locking rings or adhesives.

While FIGS. 1-3 show one complete embodiment of the invention there are modifications, refinements and other embodiments which may be made and also fall within the scope of this invention.

Figure 4:
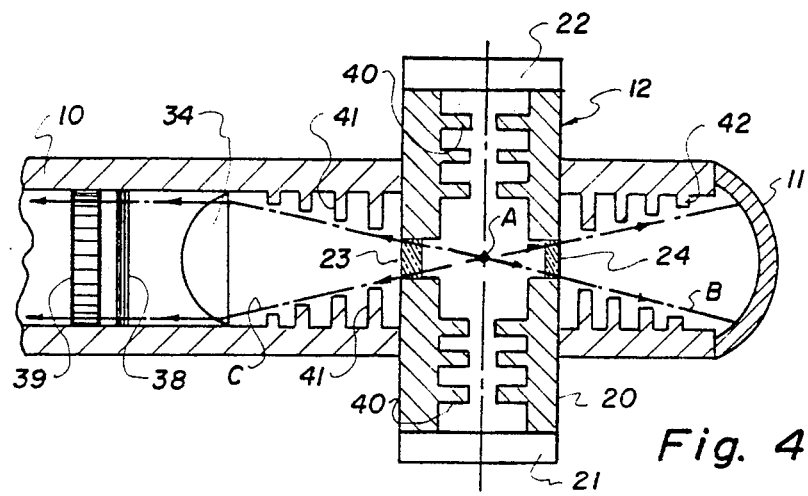
FIG. 4 is a top cross-sectional view of a gas cell and casing similar to the cell and casing of FIGS. 1 and 3 showing an embodiment using baffles to limit stray light.

One such modification is shown in FIG. 4 which is a top cross sectional view of a casing and gas cell similar to that shown in FIGS. 1-3. In order to maintain continuity and facilitate comparisons the same numerals will be used to indicate the same parts as in the previous figures although the dimensions may be somewhat different.

FIG. 4 shows, in cross section, a casing 10, into which is transversely mounted a gas cell 12 having a longitudinal housing 20. The casing axis is perpendicular to the axis of the gas cell housing 20. At one end of the casing 10 is a spherical reflection mirror 11 and at the opposite end is shown a collection lens 34, and interference filters 38 and 39 for rejecting scattered light and passing a specific Raman line on to a detector. The gas cell 12 has end windows 21 and 22 which are coated with an antireflection coating as previously described. In this embodiment, the side windows 23 and 24 are considerably smaller than those shown in FIGS. 1-3. The interior of cell housing 20 is lined with a series of circular baffles 40. Similarly, the casing 10 has a series of interior circular baffles 41 and 42 axially extending along the cell casing from either side of the cell side windows 23 and 24. Baffles 41 are located between window 23 and lens 34 and decrease in degree of interior penetration or size as they approach lens 34 thereby allowing a greater open interior diameter in the direction of lens 34. Similarly, baffles 42 are located between window 24 and mirror 11 and decrease in degree of interior penetration or size as they approach mirror 11 thereby allowing a greater open interior diameter adjacent lens 34. These baffles function to reject or reduce stray light which adds to background signal. Therefore, light collection from a specific point "A" along the laser beam path with minimal stray light is facilitated. The shape and positioning of baffles 41 and 42 allow optimal collection and reflection of scattered light by mirror 11 and collection of scattered light by lens 34 as shown by directional arrows "B" and "C" respectively.

The embodiment shown in FIG. 4 is an intracavity application made possible through the design and construction of gas cell 12.

From the above description it is obvious that the present invention presents many advantages in the field of Raman scattering analysis. For example, an expensive, high volume multi-pass cell outside the laser cavity which requires high tolerance mirrors, as disclosed in German Pat. De. No. 27 23 939 C2 has been replaced with a relatively simple gas cell, suitable for intracavity use, requiring two appropriately located end windows each preferably coated with an antireflection coating and appropriate side window cofigurations which may or may not be coated according to the desired application.

The gas cells and casing described herein were developed primarily for use in monitoring respiratory and anesthesia gases. However, they may also be useful for monitoring blood and tissue gases (in conjunction with a suitable sampling catheter), gases used for lung function and cardiac output determinations, hazardous gases in the work place, for detecting leaks in chemical process plants, for monitoring levels of suspected chemical and environmental pollutants and in other applications where polyatomic gaseous molecules are to be detected and measured.

While the above presents various working embodiments of the invention there are others which will be obvious to those skilled in the art. The invention is not to be limited to the embodiments specifically described but is to be interpreted only in conjunction with the scope of the appended claims and their functional equivalents.

I claim:

1. A sample gas cell and casing system for use in sampling and analysis of gas samples by Raman light scattering comprising in combination;

(a) a tubular casing means forming a longitudinal bore having a collection end adapted to engage into and be aligned with light collection and detection means and an opposing closed end containing reflection means consisting of a spherical or cylindrical mirror, for collecting and directing scattered light through said logitudinal bore toward said collection end.

(b) a gas sampling cell transversely mounted in said tubular casing means relative to said longitudinal bore and adjacent said closed end said gas sampling cell protruding at either end through said tubular casing and having opposing windows at the ends thereof located outside said tubular casing said end windows being positioned to be substantially parallel to each other and interconnected by a continuous sidewall passing through said tubular casing, said end windows and sidewall defining a longitudinal gas chamber having an axis perpendicular to the axis of said longitudinal bore in said tubular casing said axis of said gas cell chamber being located relative to said reflection means at a distance equal to the radius of curvature of said reflection means, at least a portion of said continuous sidewall located inside said tubular casing having window means consisting of opposing aligned side windows in said sidewall parallel to and on either side of the axis of said longitudinal gas chamber through which scattered light may pass, said gas cell further containing inlet and outlet means communicating with said chamber to pass a sample gas through said cell;

(c) said gas cell and window means being positioned in said tubular casing relative to said collection end and said reflection means to bring said side windows and said reflection means into alignment with the axis of said longitudinal bore of said tubular casing such that a portion of scattered light passing through said window means which does not pass directly to said collection end is collected by said reflection means and directed to said collection end of said tubular casing.

2. A system according to claim 1 wherein said end windows are positioned to be substantially normal to the axis of the longitudinal gas cell chamber and wherein said end windows are coated with an antireflection coating specific to a selected wavelength of a laser beam.

3. A system according to claim 1 wherein said parallel end windows are positioned at Brewster's angle.

4. A system according to claim 1 wherein the interior of said gas cell and said tubular casing contains a series of baffles to reject stray light.

5. A system according to claim 2 wherein said reflection means is a spherical mirror.

6. A system according to claim 2 wherein said reflection means is a cylindrical mirror.

7. A system according to claim 2 wherein said side windows in said gas cell are coated with a broad band antireflection coating adapted to pass desired wavelengths of inelastic Raman scattered light.

* * * * *